United States Patent [19]

Szczepanski

[11] Patent Number: 4,519,834
[45] Date of Patent: May 28, 1985

[54] HERBICIDAL ETHYNYL-PHENYLUREAS

[75] Inventor: Henry Szczepanski, Rheinfelden, Switzerland

[73] Assignee: Ciba-Geigy Corporation, Ardsley, N.Y.

[21] Appl. No.: 512,273

[22] Filed: Jul. 11, 1983

Related U.S. Application Data

[62] Division of Ser. No. 214,813, Dec. 9, 1980, Pat. No. 4,406,691.

[30] Foreign Application Priority Data

Dec. 18, 1979 [CH] Switzerland .................. 11214/79

[51] Int. Cl.³ .................. A01N 37/00; A01N 37/44; A01N 47/30; C07C 155/02
[52] U.S. Cl. .................. 71/100; 260/455 A; 260/453 RW; 564/100; 564/48; 564/50; 564/51; 564/52; 564/53; 564/54; 564/55; 71/111; 71/120; 560/29; 560/30; 560/22; 560/24; 560/27; 560/34
[58] Field of Search .... 260/455 A, 453 RZ, 453 RW; 564/100, 48, 50, 51, 52, 53, 54, 55; 71/100, 111, 71/120; 560/22, 29, 30, 24, 27, 31, 32, 34

[56] References Cited

U.S. PATENT DOCUMENTS 3,332,988  7/1967  Mull .................. 260/455 A

FOREIGN PATENT DOCUMENTS 583509  1/1977  Switzerland .................. 564/48

Primary Examiner—Henry R. Jiles
Assistant Examiner—Robert C. Whittenbaugh
Attorney, Agent, or Firm—Edward M. Roberts; Frederick H. Rabin

[57] ABSTRACT

The ethynyl-phenylureas of the formula I

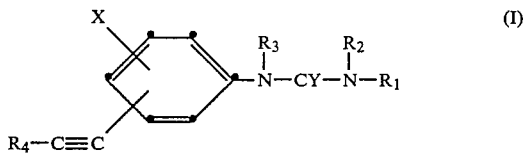

wherein X is hydrogen, halogen, lower alkyl, lower alkoxy, haloalkyl or nitro, Y is oxygen or sulfur, $R_1$ is hydrogen, alkyl, alkoxy, alkenyl, phenyl or benzyl, $R_2$ is hydrogen, alkyl, cycloalkyl, alkenyl, alkynyl or benzyl, $R_1$ and $R_2$ together with the nitrogen atom to which they are bound are also a pyrrolidine, piperidine, morpholino or piperazine ring, $R_3$ is hydrogen or lower alkyl, and $R_4$ is hydrogen, alkyl, phenyl, pyridyl, alkenyl, cycloalkyl or cycloalkenyl, are novel substances. They are characterized by strong herbicidal activity.

17 Claims, No Drawings

HERBICIDAL ETHYNYL-PHENYLUREAS

This is a division of application Ser. No. 214,813 filed on Dec. 9, 1980, now U.S. Pat. No. 4,406,691.

The present invention relates to novel ethynyl-phenylureas having herbicidal activity, to processes for their production, to compositions containing them as active substances, and to the use thereof.

The novel ethynyl-phenylureas correspond to the formula I

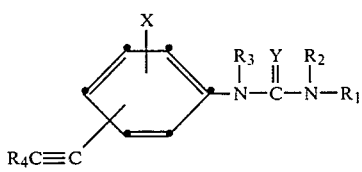

wherein X is hydrogen, halogen, $C_1$–$C_4$-alkyl, $C_1$–$C_4$-alkoxy, $C_1$–$C_4$-haloalkyl or nitro, Y is oxygen or sulfur, $R_1$ is hydrogen, $C_1$–$C_6$-alkyl, $C_1$–$C_4$-alkoxy, $C_2$–$C_6$-alkenyl, or phenyl or benzyl each unsubstituted or substituted by halogen; $R_2$ is hydrogen, $C_1$–$C_6$-alkyl, $C_3$–$C_6$-cycloalkyl, $C_2$–$C_6$-alkenyl or $C_2$–$C_6$-alkynyl, or benzyl unsubstituted or substituted by halogen; and $R_1$ and $R_2$ together with the nitrogen atom to which they are bound can also form a pyrrolidine, piperidine, morpholine or piperazine ring; $R_3$ is hydrogen or $C_1$–$C_4$-alkyl; $R_4$ is hydrogen, $C_1$–$C_{12}$-alkyl unsubstituted or substituted by hydroxyl or halogen, by unsubstituted or substituted pyranyloxy or furanyloxy groups, by $C_1$–$C_4$-alkoxy, $C_2$–$C_8$-alkoxyalkoxy or $C_1$–$C_4$-alkoxycarbonyl, or by an amino group —N($R_1$)($R_2$, —N($R_1$)COOR$_2$, —N($R_1$)COSR$_2$, —N($R_1$)CON($R_1$)R$_2$ or —CON($R_1$)R$_2$, or $R_4$ is phenyl or pyridyl each unsubstituted or substituted by halogen, $C_1$–$C_4$-alkyl, $C_1$–$C_4$-alkoxy, $C_1$–$C_4$-haloalkyl, nitro, $C_1$–$C_4$-alkylsulfonyl or by unsubstituted or substituted phenoxy, or $R_4$ is $C_2$–$C_{12}$-alkenyl unsubstituted or substituted by halogen, hydroxyl, $C_1$–$C_4$-alkoxy, $C_2$–$C_8$-alkoxyalkoxy or $C_1$–$C_4$-alkoxycarbonyl, or $R_4$ is $C_3$–$C_{12}$-cycloalkyl or -cycloalkenyl which can be mono- or bicyclic and can be substituted by halogen, hydroxyl or $C_1$–$C_4$-alkoxy.

The alkyl group $R_4$ can be straight-chain, but is advantageously a radical branched in the 1-position, which can also be substituted, for example isopropyl, 1-hydroxyisopropyl, 1-chloroisopropyl, 2-butyl, 2-hydroxybutyl radicals, and so forth.

The alkenyl groups $R_4$ are likewise preferably substituted in the 1-position, such as but-3-en-2-yl or prop-2-en-2-yl. The alkyl and alkenyl groups can be substituted by halogen or hydroxyl and/or can be once or repeatedly interrupted by oxygen bridges. Substituents of these groups include also the pyranyloxy and furanyloxy groups or a pyridyloxy group. Preferred cycloalkyl or cycloalkenyl groups are cyclopentyl, cyclohexyl and cyclohex-1-enyl. Further preferred $R_4$ groups are tertiary alkyl and alkenyl groups bound by way of one or two oxygen atoms, for example the 2-(1'-ethoxy-ethoxy)-but-2-yl group, the 3-(1'-ethoxy-ethoxy)-pent-3-yl group, and so forth:

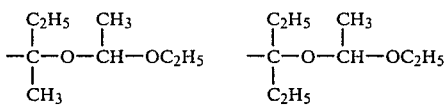

The ethynyl ureas of the formula I according to the invention influence plant growth, and exhibit in particular excellent herbicidal properties. They are used especially for combating weeds; they can however, by virtue of their advantageous desiccating and defoliating activity, be used as a means of increasing yields in crops of cotton and potatoes.

In combating mono- and dicotyledonous weeds, the active substances of the formula I have, even when applied in small amounts, an outstanding herbicidal action against undesirable plant growth whilst leaving unharmed a series of crops of productive plants, and are surprisingly superior to known phenylurea derivatives which are structurally similar. Varieties of weeds difficult to control are therefore also effectively combated by the active substances of the formula I. There results however a total-herbicidal action where the amount applied is sufficiently great. The novel active substances of the invention can be applied both in the pre-emergence process and in the post-emergence process. The applied amounts can vary within wide limits, for example between 0.1 and 10 kg of active substance per hectare, preferably however between 0.5 and 5 kg of active substance per hectare.

The compositions according to the invention contain, besides the active substance of the formula I, a suitable carrier and/or other additives. Suitable carriers and additives can be solid or liquid and correspond to the substances customarily used in formulation practice, such as natural or regenerated mineral substances, solvents, diluting, dispersing, emulsifying and wetting agents, adhesives, thickeners, binders and/or fertilisers.

For use in herbicidal compositions, a compound of the formula I can be processed, by customary formulation methods, into a dust, emulsion concentrate, granulate, dispersion, solution or suspension.

Active substances which have proved particularly active are those of the following subgroups of ethynyl-phenylureas which are all embraced by the formula I

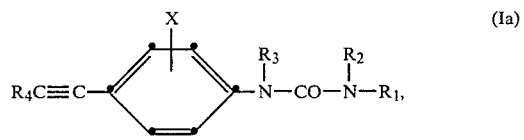

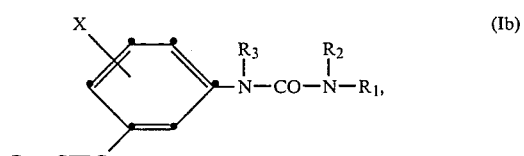

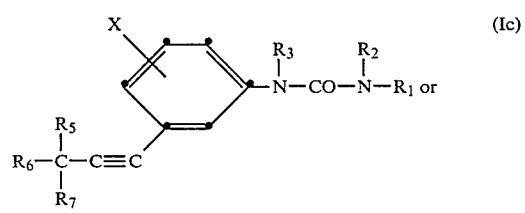

-continued

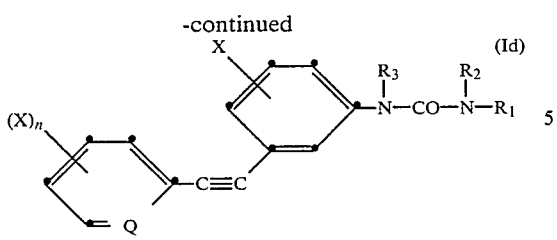

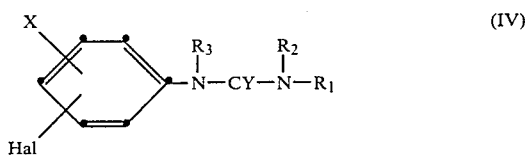

wherein $R_1$, $R_2$, $R_3$, X and Y have the meanings defined above, and "Hal" is a halogen atom, especially a chlorine, bromine or iodine atom, which is in the meta- or para-position with respect to the urea group, is reacted, in the presence of a base, with an ethynyl compound of the formula V $$R_4-C\equiv CH \qquad (V)$$

in which $R_4$ has the meaning defined above.

In these formulae, $R_1$, $R_2$, $R_3$, $R_4$ and X have the meanings defined under the formula I, $R_5$ is hydrogen, $C_1$–$C_6$-alkyl or $C_2$–$C_6$-alkenyl, $R_6$ is the same as $R_5$ or it is phenyl which is unsubstituted or substituted by halogen, $C_1$–$C_4$-alkyl, $C_1$–$C_4$-alkoxy, $C_1$–$C_4$-haloalkyl, nitro or phenoxy, $R_7$ is $C_1$–$C_6$-alkyl which is optionally once or repeatedly interrupted by oxygen or substituted by hydroxyl or halogen, Q is a carbon or nitrogen atom, and n is 0, 1, 2 or 3.

The compounds of the formula I are produced by methods known per se, for example by reaction of an ethynylphenyl derivative of the formula II

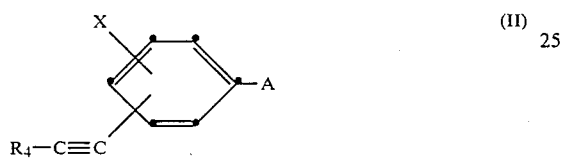

with an amine of the formula III

Instead of an ethynyl compound, there can be used in this reaction, in the presence of a strong inorganic base, such as NaOH or KOH, also a tertiary ethynyl alkanol of the formula VI

wherein $R_5$ and $R_6$ have the meanings defined above. In this reaction, a keto group $O=CR_5R_6$ is split off.

It is possible in the same manner to split off a tertiary alkanol group $R_4$ from the ethynyl group, and to react the hydrogen atom remaining, in the presence of a base, with another group, for example a halogenated group Hal $R_4$, for example with a phenyl group, corresponding to the reaction scheme

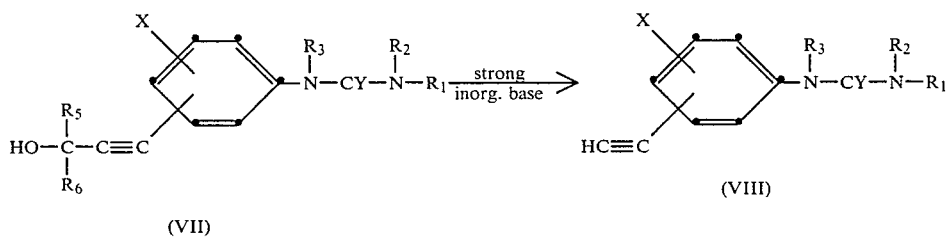

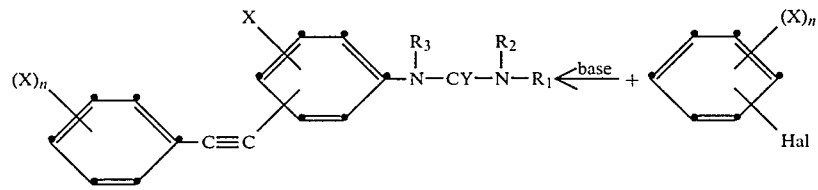

wherein $R_1$, $R_2$, $R_4$ and X have the meanings defined under the formula I, whilst A and B are radicals which form ureas as a result of addition or condensation. One of the two groups A and B is an amine, and the other is a urethane, a carbamoyl halide or a urea group, or in particular the isocyanate group.

The ethynyl-phenylureas of the formula I can be produced also by a process wherein a halogenated phenylurea of the formula IV In these formulae, $R_1$, $R_2$, $R_3$, $R_4$, $R_5$, $R_6$, X, Y, "Hal" and n have the meanings defined above.

These reactions are performed advantageously in organic solvents or solvent mixtures which are inert to the reactants. Suitable as such are many protic as well as aprotic solvents, for example alkanols, ketones, ethers, hydrocarbons or halogenated hydrocarbons, or aromatic solvents, and also for example dimethylformamide or dimethylsulfoxide.

When a halogen atom is split off in the reaction, the acid-binding agent used can be a base. Suitable bases are strong inorganic bases, such as KOH or NaOH, but also organic bases, for example trimethylamine, diethylamine, pyridine, and so forth.

Reactions in which the ethynyl group is concomitantly involved are advantageously performed in the presence of a catalyst. Suitable catalysts are in particular noble metal catalysts, which are used as such or absorbed onto a carrier, for example powdered charcoal, aluminium oxide, and the like. They can be palladium complexes which if necessary are used with the addition of copper iodide (CuI). Examples of catalysts of this type are palladium acetate Pd(OCOCH$_3$)$_2$ or the palladium-dichloro-bis-(triphenylphosphine) complex, PdCl$_2$[P(C$_6$H$_5$)$_3$]$_2$.

The temperatures of the reactions are between room temperature and the boiling point of the reaction mixture. Although reactions leading to the synthesis of the urea group generally proceed at room temperature, and those in which the ethynyl group is involved are slightly exothermic, it is nevertheless favourable to raise the temperature in the reaction vessel for a short time in order to increase the rate of reaction.

Starting products of the formula II are described for example in the German Offenlegungsschrift No. 2,905,507 and in the U.S. Pat. No. 4,128,588. To produce an aniline of the formula II (A=NH$_2$), there is reduced for example an acetylene-substituted nitrobenzene. The nitro group can be selectively hydrogenated, which is effected with special reducing agents, such as zinc, zinc salts, iron salts, sodium- and ammonium-sulfite, -dithionite or -hydrosulfite; but also by catalytic hydrogenation with special catalysts based on ruthenium or heavy metal oxides.

The starting materials of the formulae III, IV, V and VI are known, or are easy to produce and/or are commercially obtainable.

The compounds of the formula I have relatively good solubility in the customary organic solvents but poor solubility in water. They are formulated as liquid herbicidal compositions with the aid of special solubility-promoting agents and/or dispersing agents.

The novel active substances of the formula I are stable compounds which are soluble in customary organic solvents, such as alcohols, ethers, ketones, dimethylformamide, dimethylsulfoxide, and so forth.

The compositions according to the invention are produced in a manner known per se by the intimate mixing and grinding of active substances of the general formula I with suitable carriers and/or distributing agents, optionally with the addition of antifoaming agents, wetting agents, dispersing agents and/or solvents, all inert to the active substances. The active substances can be obtained and used in the following forms:

solid preparations: dusts, scattering agents, granules (coated granules, impregnated granules and homogeneous granules);

water-dispersible concentrates of active substance: wettable powders, pastes, emulsions and emulsion concentrates, and liquid preparations: solutions.

The concentration of active substance in the compositions according to the invention is 1 to 80 percent by weight, and when being applied the compositions can if necessary contain the active substance also at a lower concentration, such as about 0.05 to 1 percent by weight.

Other biocidal active substances or compositions can be mixed with the compositions according to the invention. For broadening their scope of action, the novel compositions can thus contain, besides the stated compounds of the general formula I, for example insecticides, fungicides, bactericides, fungistatics, bacteriostatics or nematocides, or further herbicides.

The Examples which follow are intended to further illustrate the production of the phenylureas of the formula I according to the invention. Further compounds produced in an analogous manner are listed in the Table which follows. The temperatures values are given in degrees Centigrade; parts and percentages are by weight, and pressure values are expressed in millibars (mbars).

EXAMPLE 1

N-[3-Chloro-4-(3'-methyl-3'-hydroxybut-1'-in-1'-yl)-phenyl]-N'-methoxy-N'-methylurea

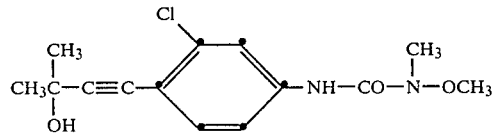

0.4 g of copper iodide and 1.6 g of palladium complex PdCl$_2$[P(C$_6$H$_5$)$_3$]$_2$ were added, under nitrogen, to a solution of 69.4 g (0.25 mol) of N-(3'-chloro-4'-bromophenyl)-N'-methoxy-N'-methylurea and 30 g (0.36 mol) of 3-hydroxy-3-methyl-1-butine in a mixture of 500 ml of triethylamine and 15 ml of dimethylformamide. The reaction mixture was heated for 24 hours at 80° C., and an amount of active charcoal was then added; the mixture was filtered with suction and concentrated by evaporation. The residue was taken up in 500 ml of ether, and washed three times with 300 ml of 5% aqueous HCl solution each time. It was subsequently dried, treated with active charcoal, filtered off with suction and concentrated by evaporation. After concentration by evaporation, there were added 200 ml of ether, and the product was allowed to crystallise. The yield was 44 g of colourless crystals of the title compound, m.p. 123°–124°.

EXAMPLE 2

N-[3-Chloro-4-(3'-methyl-but-3'-en-1'-yl)phenyl]-N'-methoxy-N'-methylurea

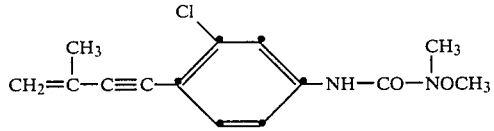

A solution of 15 g of the urea of Example 1 in 100 ml of toluene was added to 10 ml of pyridine and 5.7 g of methylsulfonyl chloride CH$_3$SO$_2$Cl at room temperature. The mixture was heated for 4 hours at 90°, subsequently diluted with 300 ml of ether, and washed twice with 250 ml of 5% HCl solution and 250 ml of 5% NaOH solution each time. Active charcoal was added to the organic phase; it was then dried, filtered, and concentrated by evaporation. The crude product was chromatographed on silica gel (eluant: methylene chloride), in the course of which 5.2 g of the title compound, m.p. 124°–125°, crystallised out from the resulting oil.

EXAMPLE 3

N-[3-(3'-hydroxy-3'-methyl-but-1'-in-1'-yl)-phenyl]-N'-methoxy-N'-methylurea

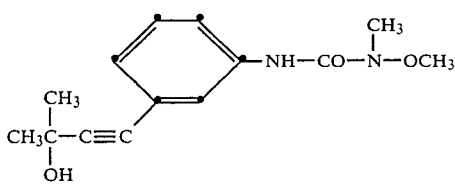

45 g of N-(3-iodophenyl)-N'-methoxy-N'-methylurea were suspended in 300 ml of triethylamine, and 0.2 g of copper iodide and 0.8 g of palladium complex PdCl$_2$[P(C$_6$H$_5$)$_3$]$_2$ were added in a nitrogen atomosphere. The reaction mixture was stirred for 14 hours at 45° and was then diluted with ether; the ether solution was subsequently washed with an aqueous acid solution as in Example 1, dried and afterwards concentrated by evaporation. The residue was crystallised from hexane to yield 30 g of the title compound, m.p. 76°–78°.

EXAMPLE 4

N-[3-(3'-Methyl-but-3'-en-1'-in-1'-yl)-phenyl]-N'-methoxy-N'-methylurea

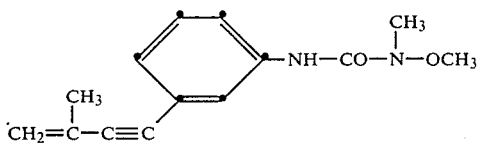

Pyridine and methylsulfonyl chloride were added to 10.5 g of the urea of Example 3 by a process analogous to that of Example 2, and the reaction mixture was heated at 90° for 4 hours. After cooling, it was evaporated to dryness, and the residue was taken up in ether. After processing, the organic phase was concentrated by evaporation, and chromatographed by means of methylene chloride through a silica gel column. The yield was 6.1 g of the title compound in the form of light-brown powder, m.p. 56°–57°.

EXAMPLE 5

N-[3-(4'-Methyl-phenyl-ethynyl)-phenyl]-N'-methoxy-N'-methylurea

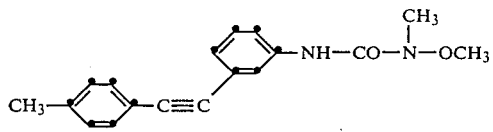

9 m of triethylamine and 6 g of methoxymethylcarbamoyl chloride were added to a solution of 11 g of (3-(4'-methylphenyl-ethynyl)-aniline in 100 ml of ether, and the reaction mixture was refluxed for 4 hours. It was subsequently washed with 150 ml of an aqueous HCl solution (5%) and with 150 ml of water and dried and the organic phase was then concentrated by evapoation. The residue was taken up in ether and crystallised. The yield was 12.5 g of the title compound, m.p. 113°.

The aniline required as intermediate was produced as follows:

(a) To a solution of 44 g of 3-iodoaniline and 20 g of 3-hydroxy-3-methyl-but-1-ine in 200 ml of triethylamine were added, in a nitrogen atmosphere, 0.3 g of copper iodide and 0.7 g of palladium complex PdCl$_2$[P(C$_6$H$_5$)$_3$]$_2$. A slight exothermic reaction occurred and the temperature rose to 55°. The reaction mixture was subsequently stirred for 12 hours at 40°, and active charcoal was added; the mixture was then filtered and concentrated by evaporation. The residue was taken up in ether, washed with 5% HCl solution and with water, dried and concentrated by evaporation. Ether was added to the residue and this was allowed to crystallise. The yield was 30 g of 3-(3'-hydroxy-3'-methyl-but-1'-in-yl)-aniline, m.p. 117°–119°.

(b) 17.5 g of the above aniline were dissolved in 100 ml of triethylamine, and 24 g of 4-iodotoluene were added. There were then added, in a nitrogen atmosphere, 0.2 g of copper iodide and 0.7 g of the palladium complex PdCl$_2$[P(C$_6$H$_5$)$_3$]$_2$ as well as 10 g of powdered KOH, and the mixture was stirred for 14 hours at 65°. Active charcoal was afterwards added to the reaction mixture, and this was filtered with suction and concentrated by evaporation. The residue was dissolved in 300 ml of ether, and the ether solution was washed three times with 250 ml of a 10% potassium carbonate solution each time. Active charcoal was added to the organic phase, and this was filtered, dried, and concentrated by evaporation. The residue was crystallised from hexane to yield 16 g of 3-(4'-methyl-phenyl-ethynyl)aniline, m.p. 88°.

EXAMPLE 6

N-{3-[4'-(2''-chloro-4''-trifluoromethylphenoxy)-phenylethynyl]-phenyl}-N'-methoxy-N'-methylurea

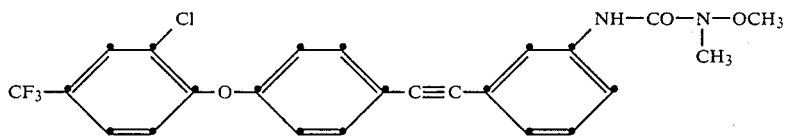

8 g of 4-(2'-chloro-4'-trifluoromethylphenoxy)-1-ethynylbenzene and 8.25 g of N-(3-iodophenyl)-N'-methoxy-N'-methylurea were suspended in 70 ml of triethylamine, and to the suspension were added, in a nitrogen atmosphere, 0.1 g of copper iodide and 0.2 g of the palladium complex PdCl$_2$[P(C$_6$H$_5$)$_3$]$_2$. A slight exothermic reaction occurred and the temperature rose to 52°. After the reaction mixture had been stirred for 2 hours at room temperature, active charcoal was added, and the mixture was filtered with suction. The filtrate was concentrated by evaporation, and the residue was taken up in ether and washed three times with 5% aqueous hydrochloric acid. The organic phase was dried, treated with active charcoal, filtered, and evaporated to dryness. The residue was crystallised from ether/hexane (1:5) to thus yield 8.1 g of the title compound, m.p. 118°–121°.

The following compounds were produced by methods analogous to those of the Examples described in the foregoing:

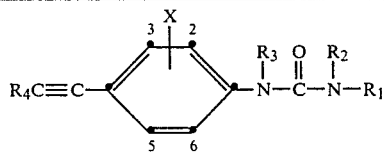

| Comp. No. | X | R₄ | R₃ | —NR₁R₂ | Phys. Data |
|---|---|---|---|---|---|
| 1.1 | — | C(CH₃)₂OH | H | N(CH₃)OCH₃ | m.p. 128–30° |
| 1.2 | — | C(CH₃)₂OCONH-phenyl | H | N(CH₃)OCH₃ | m.p. 128° (decomp) |
| 1.3 | — | C(CH₃)=CH₂ | H | N(CH₃)OCH₃ | m.p. 126° |
| 1.4 | 3-Cl | C(CH₃)₂OH | H | N(CH₃)OCH₃ | m.p. 123–124° |
| 1.5 | 3-Cl | C(CH₃)=CH₂ | H | N(CH₃)OCH₃ | m.p. 124–125° |
| 1.6 | 3-Cl | CH(CH₃)OH | H | N(CH₃)OCH₃ | m.p. 90–92° |
| 1.7 | 3-Cl | CH(CH₃)Cl | H | N(CH₃)OCH₃ | m.p. 103° |
| 1.8 | — | C(CH₃)₂OH | H | N(CH₃)₂ | m.p. 115° |
| 1.9 | — | C(CH₃)=CH₂ | H | N(CH₃)₂ | |
| 1.10 | 3-Cl | C(CH₃)OH | H | N(CH₃)₂ | |
| 1.11 | — | C(CH₃)₂OCH₃ | H | N(CH₃)OCH₃ | |
| 1.12 | — | C(CH₃)=CH₂ | H | N(CH₃)OCH₃ | oil |
| 1.13 | — | C(CH₃)(C₃H₇)OH | H | N(CH₃)OCH₃ | oil |
| 1.14 | — | CH(OH)-phenyl | H | N(CH₃)OCH₃ | oil |
| 1.15 | — | C(CH₃)₃ | H | N(CH₃)OCH₃ | |
| 1.16 | — | CH₃ | H | N(CH₃)OCH₃ | |
| 1.17 | — | -phenyl-CH₃ | H | N(CH₃)OCH₃ | |
| 1.18 | — | -phenyl | H | N(CH₃)OCH₃ | |
| 1.19 | 3-Cl | C(CH₃)₂OCHOC₂H₅ \| CH₃ | H | N(CH₃)OCH₃ | oil |
| 1.20 | — | C(C₃H₇)OCHOC₂H₇ \| CH₃ \| CH₃ | H | N(CH₃=OCH₃) | oil |
| 1.21 | — | C(CH₃)=CH₂ | H | N(C₂H₅)₂ | |
| 1.22 | — | C(CH₃)₂OH | H | N(C₂H₅)₂ | |
| 1.23 | 3-Cl | H | H | N(CH₃)OCH₃ | m.p. 103–4° |
| 1.24 | — | H | H | N(CH₃)OCH₃ | |

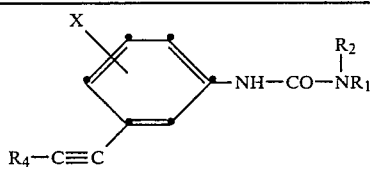

Comp.

-continued

| No. | X | R₄ | NR₁R₂ | Phys. data |
|---|---|---|---|---|
| 2.1 | — | —C(CH₃)(C₂H₅)OH | N(CH₃)(OCH₃) | m.p. 79–81° |
| 2.2 | — | —C(CH₃)(C₂H₅)OCH(CH₃)OC₂H₅ | N(CH₃)₂ | $n_D^{21}$: 1.5210 |
| 2.3 | — | —C(CH₃)=CH—CH₃ | N(CH₃)OCH₃ | oil |
| 2.4 | — | —C(CH₃)(C₂H₅)Cl | N(CH₃)OCH₃ | |
| 2.5 | — | —C(C₂H₅)₂OH | N(C₂H₅)₂ | |
| 2.6 | — | —C(C₂H₅)₂OCH(CH₃)OC₂H₅ | N(CH₃)₂ | |
| 2.7 | — | —C(C₂H₅)₂O—(tetrahydropyranyl) | N(CH₃)OCH₃ | |
| 2.8 | — | —C(C₂H₅)=CH—CH₃ | N(CH₃)₂ | oil |
| 2.9 | — | —C(C₂H₅)₂Cl | N(CH₃)OCH₃ | |
| 2.10 | — | —C(CH₃)=CH—C₂H₅ | N(CH₃)OCH₃ | |
| 2.11 | — | —C(CH₃)(C₃H₇n)Cl | N(C₂H₅)₂ | |
| 2.12 | — | —C(CH₃)(C₄H₉iso)OH | N(CH₃)OCH₃ | oil |
| 2.13 | — | —C(CH₃)(C₄H₉n)OCH(CH₃)OC₂H₅ | N(CH₃)₂ | oil |
| 2.14 | — | —C(CH₃)(C₄H₉n)O—(tetrahydropyranyl) | N(CH₃)OCH₃ | |
| 2.15 | — | —C(CH₃)(C₄H₉iso)Cl | N(CH₃)OCH₃ | |
| 2.16 | — | —C(CH₃)=CH—C₃H₇iso | N(CH₃)₂ | oil |
| 2.17 | — | —C₄H₉n | NHC₃H₇iso | |
| 2.18 | — | —CH=CH—CH₂—OH | NHC₄H₉n | |
| 2.19 | — | —CH₂OH | N(C₂H₅)₂ | |
| 2.20 | — | —CH=CH—CH₂OH | N(CH₃)₂ | |
| 2.21 | — | CH=CH—CH₂OCH(CH₃)OC₂H₅ | N(CH₃)₂ | |
| 2.22 | — | 1-hydroxycyclohexyl | N(CH₃)OCH₃ | m.p. 91–92° |
| 2.23 | | cyclohexenyl | N(CH₃)OCH₃ | m.p. 56–62° |
| 2.24 | — | 1-(OCH(CH₃)OC₂H₅)cyclohexyl | N(CH₃)OCH₃ | $n_D^{21}$: 1.5295 |
| 2.25 | — | 1,4-dioxaspiro[5.5] group | N(CH₃)₂ | |
| 2.26 | — | CH=CH₂ | N(CH₃)OCH₃ | |

-continued

| | | | |
|---|---|---|---|
| 2.27 | — | 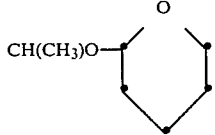 | N(C$_2$H$_5$)$_2$ |
| 2.28 | — | C(CH$_3$)(CH=CH$_2$)OH* | N(CH$_3$)$_2$ |
| 2.29 | — | C(CH$_3$)(CH=CH$_2$)Cl* | N(CH$_3$)$_2$ | *cis and trans form
| 2.30 | — | 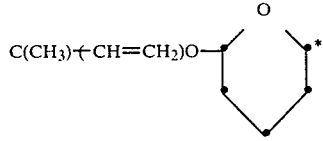 | N(CH$_3$)$_2$ |
| 2.31 | — | C(CH$_3$)=CH—CH$_2$OCH(CH$_3$)*<br>  $\quad\quad\quad\quad\quad\quad\quad\quad\quad$ \|<br>  $\quad\quad\quad\quad\quad\quad\quad\quad\quad$ OC$_2$H$_5$ | N(CH$_3$)$_2$ |
| 2.32 | — | C(CH=CH$_2$)=CH$_2$ | N(CH$_3$)OCH$_3$ |
| 2.33 | — | 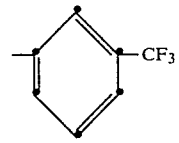 | N(CH$_3$)$_2$ |
| 2.34 | — | 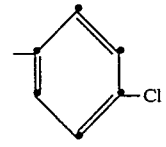 | N(CH$_3$)C$_4$H$_9$n |
| 2.35 | | 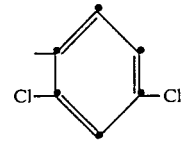 | N(OCH$_3$)CH$_3$ | m.p. 92–95°
| 2.36 | | 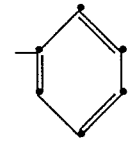 | N(CH$_3$)$_2$ | m.p. 101°
| 2.37 | — | 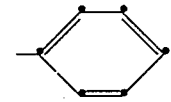 | N(CH$_3$)(OCH$_3$) | m.p. 101°
| 2.38 | — | 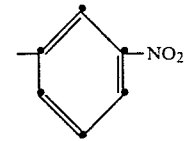 | N(CH$_3$)OCH$_3$ |
| 2.39 | — | CH(CH$_3$)$_2$OH | N(CH$_3$)CH$_2$—CH=CH$_2$ |
| 2.40 | — | CH(CH$_3$)=CHCH$_3$ | NHCH(CH$_3$)—CH=CH$_2$ |
| 2.41 | — | C(CH$_3$)$_3$ | N(CH$_3$)$_2$ |
| 2.42 | — | CH$_3$ | N(CH$_3$)OCH$_3$ | m.p 85–86°
| 2.43 | — | C$_4$H$_9$n | N(CH$_2$—CH=CH$_2$)$_2$ |
| 2.44 | — | CH$_2$OH | NHC$_4$H$_9$n |
| 2.45 | — | CH=CH$_2$ | NHC$_3$H$_7$iso |

-continued

| | | | |
|---|---|---|---|
| 2.46 | — 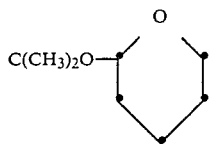 | NH(CH₃)₂ | |
| 2.47 | — 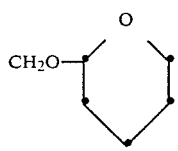 | N(CH₃)₂ | |
| 2.48 | — H | N(CH₃)OCH₃ | m.p. 77–78° |
| 2.49 | — C(CH₃)(CH=CH₂)OH | N(CH₃)OCH₃ | m.p. 64–66° |
| 2.50 | — C(CH₃)(C₄H₉iso)OCH(CH₃)C₂H₅ | N(CH₃)OCH₃ | oil |
| 2.51 | — C(CH₃)=CH—C₃H₇iso | N(CH₃)OCH₃ | oil |
| 2.52 | — CH₂OH | N(CH₃)OCH₃ | oil |
| 2.53 | — C(CH₃)=CHCH₂OH (cis) | N(CH₃)OCH₃ | m.p. 81–82° |
| 2.54 | — C(CH₃)=CHCH₂OH (trans) | N(CH₃)OCH₃ | oil |
| 2.55 | — C(CH₃)=CH₂ | N(CH₂)OCH₃ | m.p. 56–59° |
| 2.56 | — C(CH₃)=CH₂ | N(C₂H₅)₂ | m.p. 113° |
| 2.57 | — 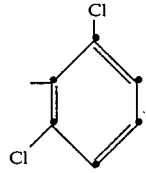 | N(CH₃)OCH₃ | m.p. 62–65° |
| 2.58 | — 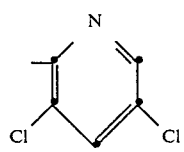 | N(CH₃)OCH₃ | m.p. 87–90° |
| 2.59 | — 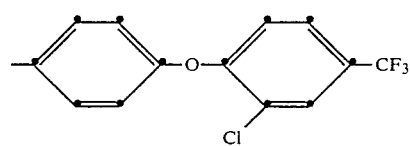 | N(CH₃)OCH₃ | m.p. 118–120° |
| 2.60 | — 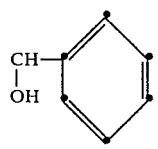 | N(CH₃)OCH₃ | oil |
| 2.61 | — C(CH₃)₃ | N(CH₃)OCH₃ | m.p. 100-2° |
| 2.62 | — C₄H₉n | N(CH₃)OCH₃ | oil |
| 2.63 | — 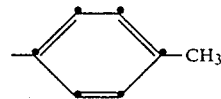 | N(CH₃)OCH₃ | m.p. 113° |
| 2.64 | — C(CH₃)₂—OCH(CH₃)OC₂H₅ | N(CH₃)OCH₃ | oil |
| 2.65 | — C(CH₃)₂OH | N(C₂H₅)₂ | m.p. 118° |
| 2.66 | — 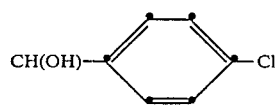 | N(CH₃)OCH₃ | oil |

-continued

| No. | R | (structure/substituent) | R' | m.p./form |
|---|---|---|---|---|
| 2.67 | — | CH(OCH₃)–C₆H₅ | N(CH₃)OCH₃ | oil |
| 2.68 | — | C(CH₃)₂O–C₆H₅ | N(CH₃)OCH₃ | oil |
| 2.69 | — | C(CH₃)₂O–C₆H₄(Cl) | N(CH₃)OCH₃ | oil |
| 2.70 | — | C(CH₃)₂—NH₂ | N(CH₃)OCH₃ | m.p. 77–80° |
| 2.71 | — | CH(CH₃)NHCH₃ | N(CH₃)OCH₃ | oil |
| 2.72 | — | CH₂N(CH₃)₂ | N(CH₃)OCH₃ | m.p. 61° |
| 2.73 | — | CH(CH₃)NH–C₆H₅ | N(CH₃)OCH | m.p. 110° |
| 2.74 | — | C(CH₃)₂NH–C₆H₂(NO₂)₂(CF₃) | N(CH₃)OCH₃ | m.p. 141° |
| 2.75 | — | C(CH₃)₂—NHCON(CH₃)OCH₃ | N(CH₃)OCH₃ | m.p. 128–132° |
| 2.76 | — | C(C₂H₅)₂NHCON(CH₃)OCH₃ | N(CH₃)OCH₃ | m.p. 89–93° |
| 2.77 | — | C(CH₃)₂NH—COSC₂H₅ | N(CH₃)OCH₃ | m.p. 102–105° |
| 2.78 | — | C(CH₃)₂NHCOOC₂H₅ | N(CH₃)OCH₃ | |
| 2.79 | — | C(CH₃)₂NH—CONHCH₃ | N(CH₃)OCH₃ | m.p. 163° |
| 2.80 | — | C(C₂H₅)₂NHCONHCH₃ | N(CH₃)OCH₃ | m.p. 110° |
| 2.81 | — | C(CH₃)₂NHCONHC₂H₅ | N(CH₃)OCH₃ | oil |
| 2.82 | — | C(CH₃)(OCH₃)CH₂CH(CH₃)₂ | N(CH₃)OCH₃ | oil |
| 2.83 | — | C(C₂H₅)OH | N(CH₃)OCH₃ | m.p. 96° |
| 2.84 | — | C₆H₄–CF₃ | N(CH₃)OCH₃ | m.p. 71° |
| 2.85 | — | C₆H₄–CH₃ | N(CH₃)OCH₃ | m.p. 85° |
| 2.86 | 4-Cl | C₆H₅ | N(CH₃)₂ | m.p. 161–163° |
| 2.87 | — | C(CH₃)₂OH | N(CH₃)₂ | m.p. 115° |
| 2.88 | 4-Cl | C(CH₃)₂OH | N(CH₃)₂ | m.p. 137° |
| 2.89 | 4-CH₃ | C(CH₃)₂OH | N(CH₃)₂ | m.p. 127° |
| 2.90 | 4-CH₃ | C(CH₃)₂OH | NHCH₃ | m.p. 146° |
| 2.91 | 4-Br | C(CH₃)₂OH | N(CH₃)₂ | |
| 2.92 | — | C₆H₅ | NHCH₃ | m.p. 172–174° |

-continued

| No. | | | m.p. |
|---|---|---|---|
| 2.93 | — | C(CH₃)(CH=CH₂)OCH(OC₂H₅)<br>                \|<br>                CH₃ | N(CH₃)OCH₃ | oil |
| 2.94 | — | C(CH₃)=CH—CH₂Cl | N(CH₃)OCH₃ | m.p. 58–60° |
| 2.95 | — | CH(CH₃)OH | N(CH₃)OCH₃ | oil |
| 2.96 | — | 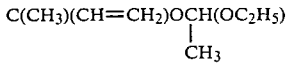 (–C₆H₄–F) | N(CH₃)OCH₃ | m.p. 97° |
| 2.97 | — |  (–C₆H₄–O–C₆H₃(Cl)(CF₃)) | N(CH₃)₂ | |
| 2.98 | — | —C(CH₃)₂NHCONHC₄H₉t. | N(CH₃)OCH₃ | m.p. 165–166° |
| 2.99 | — | —C(C₂H₅)₂NHCONHC₄H₉t. | N(CH₃)OCH₃ | m.p. 175–180° |
| 2.100 | — | —C(CH₃)₂NHCONHC₃H₇n | N(CH₃)OCH₃ | m.p. 105–110° |
| 2.101 | — | —C(C₂H₅)₂NHCONHC₃H₇n | N(CH₃)OCH₃ | m.p. 114–118° |
| 2.102 | — | 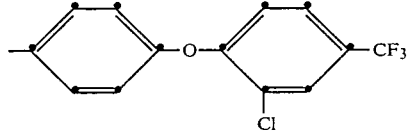 C(C₂H₅)₂NHCONH—C₆H₅ | N(CH₃)OCH₃ | |
| 2.103 | — | C(C₂H₅)₂NHCONHC₂H₅ | N(CH₃)OCH₃ | m.p. 124° |
| 2.104 | — | C(CH₃)₂NHCOOCH₃ | N(CH₃)OCH₃ | |
| 2.105 | — | 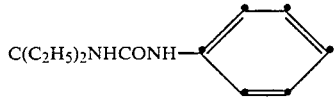 C(CH₃)₂NHCONH—C₆H₃Cl₂ | N(CH₃)OCH₃ | m.p. 180–185° |
| 2.106 | — | 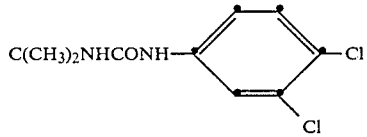 C(CH₃)₂NHCONH—(8) | N(CH₃)OCH₃ | m.p. 68–70° |
| 2.107 | — | C(CH₃)₂NHCOOCH₃ | N(CH₃)₂ | |
| 2.108 | — | C(C₂H₅)₂NHCOOC₂H₅ | N(CH₃)₂ | |
| 2.109 | — | —C(CH₃)₂NHSO₂CH₃ | N(CH₂)OCH₃ | m.p. 110–114° |
| 2.110 | — | —CH—N—CO—NOCH₃<br>    \|   \|       \|<br>   CH₃ CH₃    CH₃ | N(CH₃)OCH₃ | resin |
| 2.111 | — | C(C₂H₅)₂NHCOOC₂H₅ | N(CH₃)OCH₃ | |
| 2.112 | — | C(C₂H₅)₂NHCOOCH₃ | N(CH₃)₂ | |
| 2.113 | — | C(C₂H₅)₂NHCOOCH₃ | N(CH₃)OCH₃ | |
| 2.114 | — | C(CH₃)₂NHCOOC₄H₉iso | N(CH₃)OCH₃ | |
| 2.115 | — | C(CH₃)₂NHCOOC₄H₉n | N(CH₃)OCH₃ | |
| 2.116 | — | C(CH₃)₂NHCOOC₄H₉iso | N(CH₃)₂ | |
| 2.117 | — | C(CH₃)₂NHCOOC₄H₉n | N(CH₃)₂ | |
| 2.118 | — | C(CH₃)₂NHCOOC₃H₇iso | N(CH₃)OCH₃ | |
| 2.119 | — | C(CH₃)₂NHCOOC₃H₇iso | N(CH₃)₂ | |
| 2.120 | — | CH(CH₃)N(CH₃)COOC₂H₅ | N(CH₃)OCH₃ | |
| 2.121 | — | CH(CH₃)N(CH₃)COOCH₃ | N(CH₃)OCH₃ | |
| 2.122 | — | CH(CH₃)N(CH₃)COOC₄H₉n | N(CH₃)OCH₃ | |
| 2.123 | — | CH(CH₃)N(CH₃)COOC₃H₇iso | N(CH₃)OCH₃ | |
| 2.124 | — | C(CH₃)₂N(CH₃)COOCH₃ | N(CH₃)₂ | |
| 2.125 | — | C(CH₃)₂N(CH₃)COOC₂H₅ | N(CH₃)OCH₃ | |
| 2.126 | — | C(CH₃)₂N(CH₃)COOC₄H₉n | N(CH₃)OCH₃ | |
| 2.127 | — | C(CH₃)₂N(CH₃)COOC₃H₇iso | N(CH₃)₂ | |
| 2.128 | — | C(CH₃)₂N(CH₃)COOCH₃ | N(CH₃)OCH₃ | |
| 2.129 | — | C(CH₃)₂N(CH₃)COOC₂H₅ | N(CH₃)₂ | |
| 2.130 | — | C(CH₃)₂N(CH₃)COOC₄H₉n | N(CH₃)₂ | |
| 2.131 | — | C(CH₃)₂N(CH₃)COOC₃H₇iso | N(CH₃)OCH₃ | |

EXAMPLE 7

Production of some preparations

Granulate

The following substances are used to produce a 5% granulate:
- 5 parts of N-[3-(3'-hydroxy-3'-methylbut'-in-1'-yl)-phenyl]-N'-methoxy-N'-methylurea,
- 0.25 part of epoxidised vegetable oil,
- 0.25 part of polyethylene glycol, and
- 91 parts of kaolin (particle size: 0.3–0.8 mm).

The active substance is mixed with the vegetable oil the mixture is dissolved in 6 parts of acetone, and the polyethylene glycol and cetyl polyglycol ether are then added. The solution thus obtained is sprayed onto kaolin, and the acetone is subsequently evaporated off in vacuo.

Wettable powder

The following constituents are used to produce (a) a 70% wettable powder and (b) a 10% wettable powder:

a
- 70 parts of N-[3-(3'p-methyl-but-3'-en-1'-in-1'-yl)-phenyl]-N'-methoxy-N'-methylurea,
- 5 parts of sodium dibutyl-nalphthalene sulfonate,
- 3 parts of naphthalenesulfonic acid/phenolsulfonic acid/formaldehyde condensate (3:2:1),
- 10 parts of kaolin, and
- 12 parts of Champagne chalk; and b
- 10 parts of the above active substance,
- 3 parts of a mixture of the sodium salts of saturated fatty alcohol sulfates,
- 5 parts of naphthalenesulfonic acid/formaldehyde condensate, and
- 82 parts of kaolin.

The given active subtance is absorbed onto the appropriate carriers (kaolin and chalk), and the material is subsequently mixed and ground with the other constituents. There are thus obtained wettable powders which have excellent wetting and suspension properties, and which can be diluted with water to obtain suspensions containing 0.1–80% of active substance, these suspensions being suitable for combating weeds in crops of cultivated plants.

Paste

The following substances are used to produce a 45% paste:
- 45 parts of N-[3-chloro-4-(3'-methyl-3'-hydroxybut-1'-in-1'-yl)-phenyl]-N'-methoxy-N'-methylurea,
- 5 parts of sodium aluminium silicate,
- 14 parts of cetyl polyglycol ether having 8 mols of ethylene oxide,
- 1 part of oleyl polyglycol ether having 5 mols of ethylene oxide,
- 2 parts of spindle oil,
- 10 parts of polyethylene glycol, and
- 23 parts of water.

The active substance is intimately mixed and ground with the additives in apparatus suitable for the purpose. There is obtained a paste from which can be produced, by dilution with water, suspensions of the desired concentration.

Emulsion concentrate

The following constituents are mixed together to produce a 25% emulsion concentrate:
- 25 parts of N-[3-(4'-methylphenylethynyl)-phenyl]-N'-methoxy-N'-methylurea,
- 5 parts of a mixture of nonylphenolpolyoxyethylene and calcium dodecylbenzene sulfonate,
- 15 parts of cyclohexanone, and
- 55 parts of xylene.

This concentrate can be diluted with water to give emulsions of suitable concentration, for example 0.1 to 10%. Emulsions of this type are suitable for combating weeds in crops of cultivated plants.

EXAMPLE 8

Testing of the herbicidal action

Pre-emergence herbicidal action (inhibition of germination)

Immediately after sowing of the test plants in pots in a greenhouse, the surface of the soil was sprayed with an aqueous dispersion of the active substance, which had been prepared from a 25% emulsion concentrate, and from a 25% wettable powder containing active substance which could not be prepared as an emulsion concentrate owing to inadequate solubility, respectively. Varying concentrations were used, and the amount of active substance was calculated in kg per hectare. The pots were then kept in a greenhouse at 22°–25° with 50–70% relative humidity, and were regularly watered. The test results were evaluated after 3 weeks.

Post-emergence herbicidal action (contact herbicide)

A considerable number of weeds and of cultivated plants, both monocotyledonous and dicotyledonous, were grown in pots in a greenhouse, and were sprayed after emergence (in the 4- to 6-leaf stage) with an aqueous active-substance dispersion in varying dosages, expressed in kg of active substance per hectare; and the plants were then kept at 24°–26° with 45–60% relative humidity. The test was evaluated two weeks after the treatment.

With an applied amount of 4 kg/hectare, the compounds of the formula I exhibited a strong herbicidal action, both in the pre-emergence process and in the post-emergence process.

What is claimed is:

1. An ethynylphenylurea of the formula

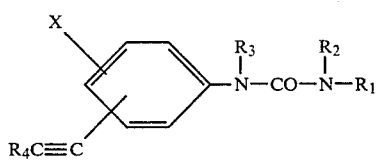

wherein
- $R_1$ is hydrogen; $C_1$–$C_6$-alkyl; $C_1$–$C_6$-alkoxy; $C_2$–$C_6$-alkenyl; phenyl optionally substituted by halogen; or benzyl optionally substituted by halogen;
- $R_2$ is hydrogen; $C_1$–$C_6$-alkyl; $C_3$–$C_6$-cycloalkyl; $C_2$–$C_6$-alkenyl; or benzyl optionally substituted by halogen;
- $R_3$ is hydrogen or $C_1$–$C_4$-alkyl;
- $R_4$ is hydrogen; $C_1$–$C_{12}$-alkyl optionally substituted by hydroxy, halogen, $C_1$–$C_4$-alkoxy, $C_2$–$C_8$-alkoxyalkoxy, $C_1$–$C_4$-alkoxycarbonyl, —N($R_1$)($R_2$), —N($R_1$)COO$R_2$, —N($R_1$)COS$R_2$ —N($R_1$)CON($R_1$)($R_2$); $C_2$–$C_{12}$-alkenyl optionally substituted by halogen, hydroxy, $C_1$–$C_4$-alkoxy, $C_2$–$C_8$-alkoxyalkoxy or $C_1$–$C_4$-alkoxycarbonyl; $C_3$–$C_{12}$-cycloalkyl or cycloalkenyl, which is mono-or bicyclic and which can be substituted by halogen, hydroxy or $C_1$–$C_4$-alkoxy; and X is hydrogen; halogen; $C_1$–$C_4$-alkyl; $C_1$–$C_4$-alkoxy; or nitro.

2. An ethynylphenylurea according to claim 1 of the formula

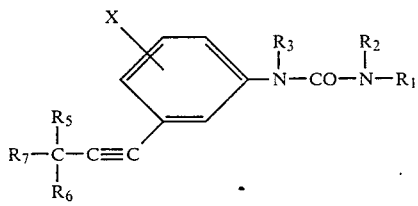

wherein $R_5$ is hydrogen; $C_1$–$C_6$-alkyl; or $C_2$–$C_6$-alkenyl;

$R_6$ is hydrogen; $C_1$–$C_6$-alkyl; $C_2$–$C_6$-alkenyl; or phenyl optionally substituted by halogen, $C_1$–$C_4$-alkyl, $C_1$–$C_4$-haloalkyl, nitro or phenoxy;

or $R_5$ and $R_6$ together can also form a $C_3$–$C_{12}$-cycloalkyl or cycloalkenyl radical, which is mono- or bicyclic and which can be substituted by halogen, hydroxy or $C_1$–$C_4$-alkyl; and $R_7$ is hydroxy; or $C_1$–$C_6$-alkyl, which is optionally once or twice interrupted by oxygen or which is substituted by hydroxy or halogen.

3. An ethynylphenylurea according to claim 1 of the formula

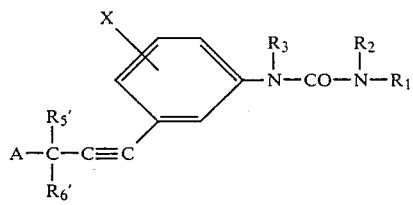

wherein each of $R_5'$ and $R_6'$ are hydrogen or $C_1$–$C_6$-alkyl; and

A is a group —N($R_1$)($R_2$), —N($R_1$)COO$R_2$, —N($R_1$)COS$R_2$, —N($R_1$)CON($R_1$)($R_2$) or —CON($R_1$)($R_2$).

4. N-(3-Ethynylphenyl)-N'-methoxy-N'-methylurea according to claim 1 of the formula

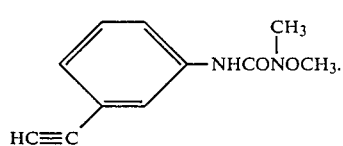

5. N-(3-Prop-1'-yn-1'-ylphenyl)-N'-methoxy-N'-methylurea according to claim 2 of the formula

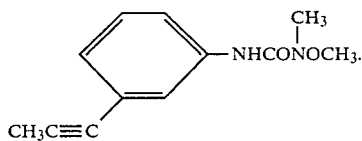

6. N-[3-(4',4'-Dimethylbut-1'-yn-1'-yl)phenyl]-N'-methoxy-N-methylurea according to claim 2 of the formula

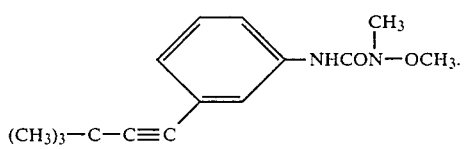

7. N-[3-(3'-Methyl-3'-hydroxy-but-1'-yn-1'-yl)phenyl]-N'-methoxy-N'-methylurea according to claim 2 of the formula

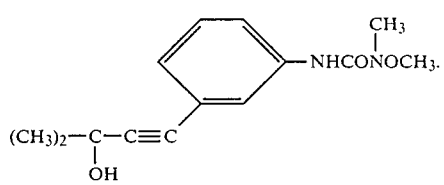

8. N-[3-(3'-Methyl-3'-hydroxy-but-1'-yn-1'-yl)phenyl]-N',N'-dimethylurea according to claim 2 of the formula

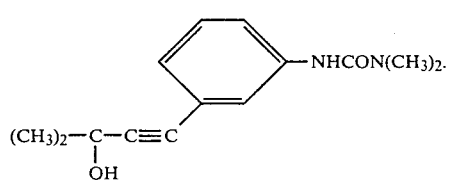

9. N-[3-(3'-Methyl-3'-hydroxy-but-1'-yn-1'-yl)-4-methylphenyl]-N'-methylurea according to claim 2 of the formula

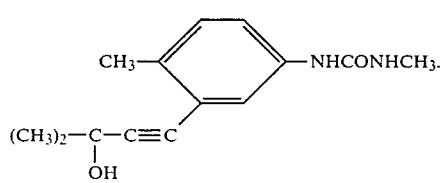

10. N-[3-(3',3'-Dimethyl-3'-ethoxycarbamoylprop-1'-yn-1'-yl)-phenyl]-N'-methoxy-N'-methylurea according to claim 3 of the formula

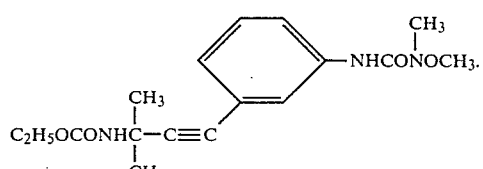

11. N-[4-(3'-Hydroxy-3'-methylhex-1'-yn-1'-yl)-phenyl]-N'-methoxy-N'-methylurea according to claim 2 of the formula

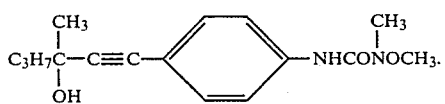

12. A herbicidal composition containing as active ingredient a herbicidally effective amount of at least one ethynylphenylurea of claim 1 and a carrier.

13. A method for combating undesirable plant growth which comprises applying thereto a herbicidally effective amount of an ethynylphenylurea of claim 1.

14. A method for selectively combating weeds in crops of cultivated plants which comprises applying to the crops to be protected a herbicidally effective amount of an ethynylphenylurea of claim 1.

15. A method for dessication and defoliation of cotton and potato plants, shortly before harvesting, which comprises applying to the plants a herbicidally effective amount of an ethynylphenylurea of claim 1.

16. A method for selectively combating weeds in cotton and sugar beet crops which comprises applying to the crops to be protected a herbicidally effective amount of an ethynylphenylurea of claim 1.

17. A method for selectively combating weeds in cereal crops which comprises applying to the crops to be protected a herbicidally effective amount of an ethynylphenylurea of claim 1.

* * * * *